United States Patent [19]

Feinberg

[11] Patent Number: 5,020,554
[45] Date of Patent: Jun. 4, 1991

[54] DENTAL FLOSS DISPENSER AND APPLICATOR

[76] Inventor: Andrew S. Feinberg, P.O. Box 12279, El Paso, Tex. 79913

[21] Appl. No.: 433,243

[22] Filed: Nov. 8, 1989

[51] Int. Cl.⁵ ............................................. A61C 15/00
[52] U.S. Cl. .................................. 132/323; 132/324; 132/327
[58] Field of Search ............... 132/323, 324, 325, 326, 132/327

[56] References Cited

U.S. PATENT DOCUMENTS

| | | | |
|---|---|---|---|
| 1,640,607 | 8/1927 | Kitley. | |
| 1,970,575 | 8/1934 | Reitzel | 132/327 |
| 2,381,530 | 8/1945 | Dembenski | 132/325 |
| 2,450,635 | 10/1948 | Dembenski | 132/325 |
| 2,577,597 | 12/1951 | Wright et al. | 132/91 |
| 2,664,093 | 12/1953 | Carpenter | 132/323 |
| 3,592,203 | 7/1971 | Johnson | 132/323 |
| 3,734,107 | 5/1973 | Thierman | 132/92 A |
| 3,746,017 | 7/1973 | Caselman | 132/92 A |
| 3,759,274 | 9/1973 | Warner | 132/325 X |
| 3,861,406 | 1/1975 | Stitt | 132/325 X |
| 3,927,687 | 12/1975 | Thierman | 132/92 A |
| 4,586,521 | 5/1986 | Urso | 132/323 X |
| 4,637,412 | 1/1987 | Martinez | 132/323 |
| 4,788,990 | 12/1988 | Wisegerber | 132/324 |

*Primary Examiner*—Gene Mancene
*Assistant Examiner*—Nicholas D. Lucchesi
*Attorney, Agent, or Firm*—Pollock, VandeSande & Priddy

[57] ABSTRACT

A dental floss holder and applicator having a hollow handle for holding a supply of dental floss and a pair of intermeshing gear wheels mounted within the handle for advancing dental floss through a pathway which includes a dental floss anchoring member, a pair of prongs for holding a section of dental floss in position for use and a pair of intermeshing gears in the handle for pulling the dental floss through the pathway. The intermeshing gears are provided with a pawl for preventing the gears from reversing direction. The intermeshing gears not only advance the dental floss, but, in cooperation with the dental floss anchoring member, maintain it in tension while the floss is in use.

12 Claims, 1 Drawing Sheet

U.S. Patent   June 4, 1991   5,020,554
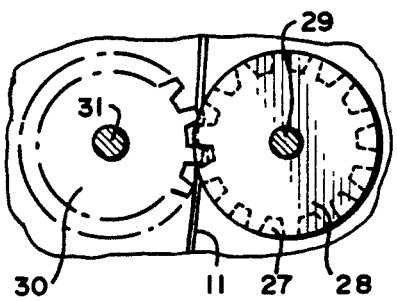
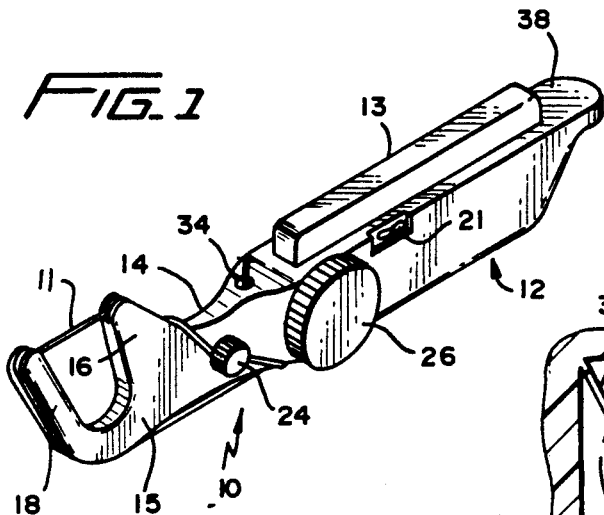
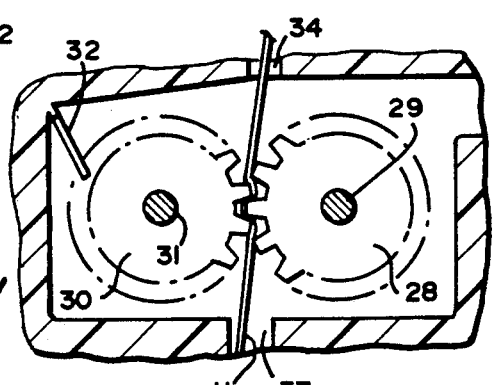
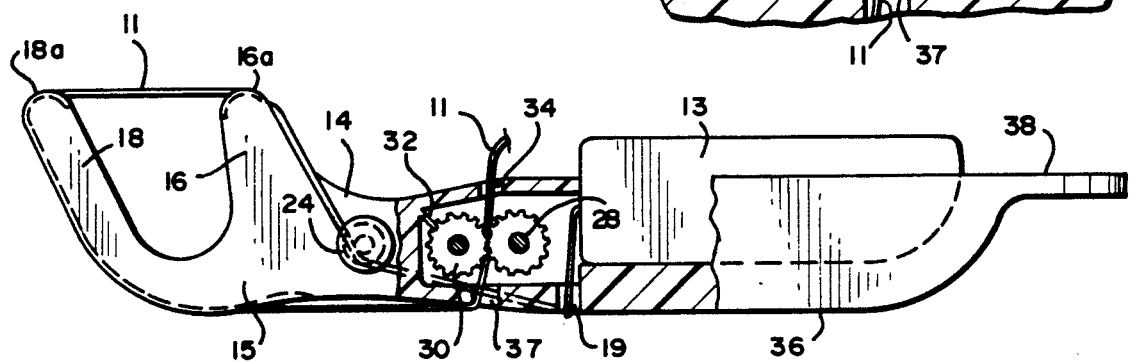
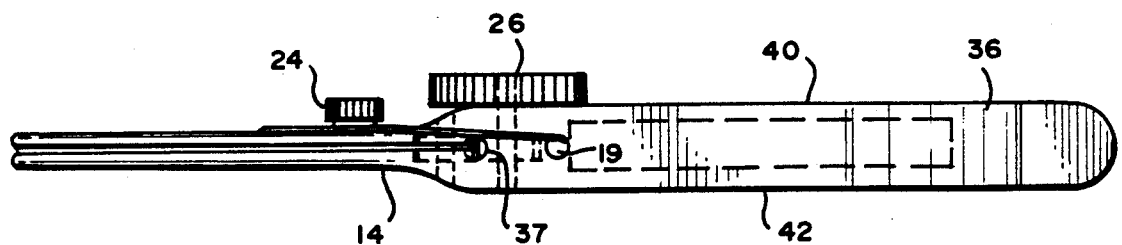

DENTAL FLOSS DISPENSER AND APPLICATOR

The present invention relates to a dental floss dispenser and applicator.

BACKGROUND OF THE INVENTION

Dental floss is usually supplied in spools, and for use a short length is cut from the spool, wrapped around fingers of opposite hands, and inserted into the mouth and between the teeth. The manipulation of floss between the teeth with the fingers is difficult, and the need for a sufficient length of floss to wrap around the fingers results in the waste of a substantial amount of floss. Devices for holding floss for use in the mouth have been proposed; however, the prior art devices have not been entirely satisfactory, and a floss holder which is convenient and easy to use, which provides proper tension on the floss, and which includes a mechanism for the positive advance of floss to replace used portions of floss with fresh portions would be an improvement over the prior art devices.

SUMMARY OF THE INVENTION

It is accordingly one object of this invention to provide an improved dental floss dispenser and applicator. Other objects of this invention are to provide a dental floss dispenser and applicator which is easy to use, does not waste floss, provides adequate tension on the floss, and includes a simple, yet effective mechanism for advancing the floss.

In accordance with this invention, there is provided a dental floss dispenser and applicator comprising a hollow handle for storing a supply of dental floss, an axially extending shank attached to one end of the handle, dental floss anchoring means mounted on the shank, and a U-shaped fork attached to the shank wherein the fork comprises a pair of curved prongs having notched tips for holding dental floss in position for applying the dental floss to the teeth. A pair of intermeshing gear wheels are rotatably mounted within the handle for advancing a strand of dental floss which has been inserted between the meshing teeth of the gears. The intermeshing gear wheels are rotated by means which are mounted on the handle, and pawl means are provided to prevent reverse rotation of the gear wheels. The pathway for the strand of dental floss extends from the supply of dental floss, past the floss anchoring means, between the tips of the prongs and back past the shank and into the handle where it passes between the gear teeth of the intermeshing gear wheels.

The present invention provides a simple apparatus and method for securing dental floss under tension during use, while at the same time providing a positive feed of the floss from a supply in the handle.

BRIEF DESCRIPTION OF THE DRAWINGS

FIG. 1 is a view in perspective of an embodiment of the dental floss holder and applicator of present invention.

FIG. 2 is a side view of the embodiment of the present invention which is shown in FIG. 1.

FIG. 3 is a bottom plan view of the embodiment of the present invention which is shown in FIG. 1.

FIG. 4 is an enlarged side view of gear wheels for advancing floss for the dental floss holder and applicator of the present invention.

FIG. 5 is a side view of another embodiment of the gear wheels for advancing floss.

DETAILED DESCRIPTION OF THE INVENTION

Referring now to the drawings, dental floss dispenser and applicator 10 comprises a hollow handle 12 having a top wall 38, a bottom wall 36 and side walls 40, 42. A shank portion 14 connects the hollow handle 12 with an applicator head 15 provided with inner and outer prongs 16 and 18, respectively. Cartridge 13 which carries a supply of dental floss is secured in hollow handle 12. The specific means for holding floss which is stored in the handle is not a part of this invention and the floss may be wound on a spool or packed loosely within the handle, or it may be held within a replaceable cartridge, as shown.

The path of movement of the strand of floss 11 is as follows. From a storage space in cartridge 13, the floss passes outwardly through an aperture 19 in the bottom wall 36 of handle 12 past floss anchoring means 24, along a groove on the outer edge of inner prong 16 to tip 16a, across the gap between prongs 16a and 18a to tip 18a, back along a groove on the outer edge of prong 18 and the bottom of shank 14 to an opening 37 in hollow handle 12 leading to intermeshing gear wheels 28, 30.

Floss anchoring means 24 is mounted on shank 14 and may, for example, comprise a knob-like protrusion around which the floss may be wound to secure it in place; however, in a preferred embodiment of the invention, the anchoring means comprises a thumbscrew-washer combination. In this embodiment of the invention, the floss is positioned between a washer and the outer surface of shank portion 14 where it is pinched by tightening the thumbscrew.

The floss which passes over tips 16a, 18a of prongs 16 and 18 and then back towards handle 12 is fed upwardly through an opening 37 in bottom wall 36 of handle 12, between meshing gear wheels 28, 30, and through opening 34 in upper wall 38. Shafts 29 and 31 for driving gear wheels 28, 30 are supported at their ends by sockets, indentations or openings in walls 40, 42. Floss advancing wheel 26 drives shaft 29 which in turn rotates intermeshing gears 28, 30.

Used floss is replaced with fresh floss by loosening floss anchoring means 24 sufficiently to permit the strand of floss to be advanced. Advancing wheel 26 is then turned in a clockwise direction, and the frictional engagement of the floss with the teeth of the gear wheels pulls the strand of floss upwardly between lower opening 37. When the desired amount of fresh floss has been moved in position between tips 16a and 18a of prongs 16 and 18, floss anchoring means 24 is tightened to prevent floss from slipping. The floss advancing wheel 26 is then turned until the floss is under sufficient tension for use. Pawl 32 engages teeth in gear wheel 30 to prevent the tension on the floss from reversing the direction of rotation of intermeshing gear wheels 28, 30. Floss cutting means 21 is provided on sidewall 42.

The meshing gear wheels 28, 30 may be made of a variety of materials, either metal or plastic, but preferably are made of a plastic such as, for example, nylon. The tooth contour and the clearance between the meshing gear wheels is not critical; however, the clearance should be adequate to permit floss to pass therebetween without binding the gears. The relatively large area of contact between the floss and the teeth provides sufficient friction to prevent the floss from slipping relative to the teeth.

In the preferred embodiment of the invention, the intermeshing gear wheels are structured to keep the floss in place between them. This may be accomplished by having the gear wheels sufficiently wide to extend substantially from one sidewall to the other; however, the dental floss may be retained in place even with relatively narrow gear wheels, i.e., wheels as narrow as about 0.1 inch or narrower, by positioning outlet aperture 34 directly above inlet aperture 37 and centered above the intermeshing gear wheels.

In one embodiment of the invention, one of the gear wheels is provided with a flange on each side for retaining the floss between the meshing teeth of the gear wheels. This embodiment is illustrated by FIG. 5 which shows flange 27 on the near side of gear wheel 28. Another flange, not shown, is provided on the far side of gear wheel 28.

The device of the present invention is also provided with a floss cutter 21 which is attached to wall 42 of handle 12, for cutting excess floss which has been pulled up between the gear wheels.

The handle 12, shank 14 and head 15 are preferably an integral element which most preferably is formed from a plastic material such as polyethylene, polypropylene, polyvinyl chloride or polyethylene terephthalate.

Modifications to the present invention will be obvious to a worker skilled in the art without departing from the scope of the invention as set forth in the following claims.

What is claimed is:

1. A dental floss dispenser and applicator comprising:
   (a) a hollow handle having a supply of dental floss;
   (b) an axially-extending shank attached to one end of said handle;
   (c) dental floss anchoring means mounted on said shank;
   (d) a U-shaped fork integral with said shank, said U-shaped fork comprising a pair of curved prongs having notched tips for holding the dental floss in position for applying said dental floss to teeth;
   (e) a pair of axially spaced-apart, contra-rotatable, intermeshing gear wheels, each wheel having outwardly extending teeth on its periphery, said wheels being rotatably mounted within said handle for advancing the dental floss inserted between the meshing teeth of said gears;
   (f) means mounted on said handle for rotating said pair of gear wheels and thereby advancing the floss positioned therebetween;
   (g) pawl means mounted in said handle and operatively connected to one of said gear wheels to prevent reverse rotation of said pair of gear wheels; and
   (h) a pathway for said dental floss extending from said supply of dental floss along said shank, past said dental floss anchoring means, between the tips of said prongs and back along said shank and between said pair of intermeshing gear wheels.

2. A dental floss dispenser and applicator according to claim 1 wherein said dental floss is provided in said handle in a replaceable cartridge.

3. A dental floss dispenser and applicator according to claim 1 wherein said dental floss anchoring means comprises a friction locking device.

4. A dental floss dispenser and applicator according to claim 3 wherein said friction locking device comprises a thumbscrew threadably mounted on said shank for clamping floss between two surfaces.

5. A dental floss dispenser and applicator according to claim 1 wherein said pair of intermeshing gear wheels is made from a plastic.

6. A dental floss dispenser and applicator according to claim 1 wherein said gear wheels each extends substantially across the width of said handle.

7. A dental floss dispenser and applicator according to claim 1 wherein said pair of intermeshing gear wheels include means for retaining said floss between said wheels.

8. A dental floss dispenser and applicator according to claim 7 wherein said means for retaining floss between gear wheels comprises flange means on one of said gear wheels.

9. A dental floss dispenser and applicator according to claim 1 wherein said handle, shank, and U-shaped fork comprise an integral element.

10. A dental floss dispenser and applicator according to claim 9 wherein said integral element is a plastic element.

11. A dental floss dispenser and applicator according to claim 1 wherein each of said pair of intermeshing gear wheels is mounted on a shaft in said handle.

12. A dental floss dispenser and applicator according to claim 11 wherein said means for rotating said pair of gear wheels comprises a driving wheel which is mounted adjacent an outer surface of a side wall of said hollow handle and secured to one of said shafts.

* * * * *